US006399758B1

(12) United States Patent
Sandrin et al.

(10) Patent No.: US 6,399,758 B1
(45) Date of Patent: *Jun. 4, 2002

(54) NUCLEIC ACIDS FOR REDUCING CARBOHYDRATE EPITOPES

(75) Inventors: Mauro Sergio Sandrin; Ian Campbell Farquhar McKenzie, both of Brunswick (AU)

(73) Assignee: The Austin Research Institute (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,077

(22) PCT Filed: Aug. 22, 1997

(86) PCT No.: PCT/AU97/00540

§ 371 Date: Jun. 11, 1999

(87) PCT Pub. No.: WO98/07837

PCT Pub. Date: Feb. 26, 1998

(30) Foreign Application Priority Data

Aug. 23, 1996 (AU) ............................................. PO 1823

(51) Int. Cl.[7] .......................... C07H 21/02; C12P 21/06; C12P 21/04; A01N 63/00; A01N 65/00
(52) U.S. Cl. ..................... 536/23.2; 435/69.1; 435/70.1; 435/455; 424/93.2; 424/93.21
(58) Field of Search .............................. 435/320.1, 325, 435/455, 69.1, 70.1; 424/93.2, 93.21; 536/23.2; 514/44

(56) References Cited

FOREIGN PATENT DOCUMENTS

WO WO 95/34202 * 12/1995

OTHER PUBLICATIONS

Federhen et. al., infro@ncbi.nlm.nih.gov.*
Anderson, "Human gene therapy", Nature, 392(Supp.):25–30, Apr. 1998.*
Verma and Somia, "Gene therapy–promises, problems and prospects", Nature, 389:239–242, Sep. 1997.*
Gillespie et al., "Cloning and expression of the Gal beta 1,3GaINAc alpha 2,3–sialytransferase", J. Biol. Chem., 267(29):21004–21010, Oct. 1992.*
Williams et al., "Large–scale expression of recombinant sialytransferases and comparison of their kinetic properties with native enzymes", Glycoconj. J., 12(6):755–761, Dec. 1995.*
Hitoshi et al., "Molecular cloning and expression of two types of rabbit beta–galactosidase alph 1,2–fucosyltransferase", J. Biol. Chem., 270(15):8844–8850, Apr. 1995.*
Sandrin et al., "Enymatic remodelling of the carbohydrate surface of a xenogenic cell substantially reduces human antibody binding and complement–mediated cytolysis", Nat. Med., 1(12):1261–1267, Dec. 1995.*
Kelly et al., "Sequence and expression of a candidate for the human secretor blood group alpha(1,2)fucosyltransferase gene (FUT2)", J. Biol. Chem., 270(9):4640–4649, Mar. 1995.*

* cited by examiner

Primary Examiner—Deborah Crouch
Assistant Examiner—Joseph T. Woitach
(74) Attorney, Agent, or Firm—Merchant & Gould P.C.

(57) ABSTRACT

The invention provides nucleic acids that encode a first glycosyltransferase that competes with a second enzyme for a substrate, thereby reducing the formation of a product of the second enzyme. The nucleic acids are useful in producing cells and organs with reduced antigenicity and which may be used for transplantation.

18 Claims, 6 Drawing Sheets

Porcine Secretor Sequence

| | M | L | S | M | Q | A | S | F | F | P | T | G | P | F | I | L | |
|---|---|---|---|---|---|---|---|---|---|---|---|---|---|---|---|---|---|
| CT | ACA | GCC | ATG | CTC | AGC | ATG | CAG | GCA | TCC | TTC | TTC | CCC | ACG | GGT | CCC | TTC | ATC | CTC |

| F | V | F | T | A | S | T | I | F | H | L | Q | Q | R | M | V | K | I | Q | P 37 |
|---|---|---|---|---|---|---|---|---|---|---|---|---|---|---|---|---|---|---|---|
| TTT | GTC | TTC | ACG | GCT | TCC | ACC | ATA | TTT | CAC | CTT | CAG | CAG | AGG | ATG | GTG | AAG | ATT | CAA | CCC |

| T | W | E | L | Q | M | V | T | Q | E | T | P | S | S | P | I | Q | L |
|---|---|---|---|---|---|---|---|---|---|---|---|---|---|---|---|---|---|
| ACG | TGG | GAG | TTA | CAG | ATG | GTG | ACG | CAG | GAG | ACA | CCC | AGC | TCG | CCC | ATT | CAG | CTG |

| K | G | M | W | T | I | N | A | L | G | R | M | Q | N | G | E | Y | A |
|---|---|---|---|---|---|---|---|---|---|---|---|---|---|---|---|---|---|
| AAG | GGC | ATG | TGG | ACG | ATC | AAT | GCC | CTG | GGG | CGC | ATG | CAG | AAC | GGG | GAG | TAC | GCC |

| T | L | Y | A | L | R | M | N | G | R | P | A | F | I | P | E | M | H |
|---|---|---|---|---|---|---|---|---|---|---|---|---|---|---|---|---|---|
| ACC | CTG | TAC | GCG | CTG | AGG | ATG | AAC | GGG | CGG | CCG | GCC | TTC | ATC | CCG | GAG | ATG | CAC |

| S | T | L | A | P | I | F | R | I | T | L | P | V | L | H | A | S | T | A | R 117 |
|---|---|---|---|---|---|---|---|---|---|---|---|---|---|---|---|---|---|---|---|
| AGC | ACG | CTG | GCC | CCC | ATC | TTC | AGG | ATC | ACC | CTC | CCG | GTC | CTG | CAC | GCC | AGC | ACG | GCC | CGC |

| R | I | P | W | Q | N | Y | H | L | D | W | M | E | R | Y | R | H | I |
|---|---|---|---|---|---|---|---|---|---|---|---|---|---|---|---|---|---|
| AGG | ATC | CCC | TGG | CAG | AAC | TAC | CAC | CTG | GAC | TGG | ATG | GAG | CGG | TAC | CGC | CAC | ATC |

| P | G | E | Y | V | R | L | T | G | Y | P | C | S | W | T | F | Y | H | L |
|---|---|---|---|---|---|---|---|---|---|---|---|---|---|---|---|---|---|---|
| CCG | GGG | GAG | TAC | GTG | CGC | CTC | ACG | GGC | TAC | CCC | TGC | TCC | TGG | ACC | TTC | TAC | CAC | CTG |

| R | T | E | I | L | R | E | F | T | L | H | N | H | V | R | E | E | A | Q | D |
|---|---|---|---|---|---|---|---|---|---|---|---|---|---|---|---|---|---|---|---|
| CGC | ACC | GAG | ATC | CTC | CGG | GAG | TTC | ACC | CTG | CAT | AAC | CAC | GTG | CGC | GAG | GAG | GCC | CAG | GAT |

```
F   L   G   L   R   V   N   G   S   R   P   S   T   Y   V   G   V   H   V
TTC CTG GGT CTG CGG GTG AAC GGG AGC CGA CCG AGT ACC TAC GTG GGG GTG CAC GTG

R   R   G   D   Y   V   H   V   M   P   N   V   W   K   G   V   V   A   D   R
CGC CGG GGG GAC TAC GTG CAC GTG ATG CCC AAC GTG TGG AAG GGC GTG GCC GAC CGG

R   Y   L   E   Q   A   L   D   W   F   R   A   R   Y   S   P   V   F   V
CGG TAC CTG GAG CAG GCC CTG GAC TGG TTC CGG GCT CGC TAC TCC CCC GTC TTT GTG

V   S   N   G   M   A   C   W   R   E   N   I   N   A   S   R   A   L   D   V
GTC TCC AGC AAC ATG GCC TGT TGG CGG GAA AAT ATC AAT GCC TCG CGC GCC CTC GAT GTG

V   F   A   G   N   G   I   G   T   F   G   I   W   A   A   F   L   K   L   Q
GTG TTT GCC GGC AAT GGC ATC GGC ACG TTC GGG ATC TGG GCC GCC TTC CTC AAA CTC CAG

C   N   H   T   V   M   T   I   Y   N   Y   T   A   Y   L   A   L   T   A   G
TGT AAC CAC ACT GTC ATG ACC ATT GGC TAC AAT TAC ACG GCC TAC CTT GCT ACG GCT GGT

G   E   T   I   Y   L   A   A   F   L   P   D   S   P   F   L   K   L   F
GGA GAG ACC ATC TAC CTG GCC GCC TTC CTC CCG GAC TCT CCC TTC CTC CTC AAA CTC TTT

K   P   E   A   F   L   P   E   W   I   G   I   E   A   D   L   S   P   L
AAG CCC GAG GCA GCC TTC CTG CCC GAG TGG ATT GGG ATC GAG GCA GAC CTG TCC CCA CTC

L   K   H   *
CTT AAG CAC TGA TGT CGG CTG TCC (SEQ. ID NO: 6)
(SEQ. ID NO: 5)
```

NUCLEIC ACIDS FOR REDUCING CARBOHYDRATE EPITOPES

The present invention relates to nucleic acids which encode glycosyltransferase and are useful in producing cells and organs from one species which may be used for transplantation into a recipient of another species. Specifically the invention concerns production of nucleic acids which, when present in cells of a transplanted organ result in reduced levels of antibody recognition of the transplanted organ.

The transplantation of organs is now possible due to major advances in surgical and other techniques. However, availability of suitable human organs for transplantation is a significant problem. Demand outstrips supply. This has caused researchers to investigate the possibility of using non-human organs for transplantation.

Xenotransplantation is the transplantation of organs from one species to a recipient of a different species. Rejection of the transplant in such cases is a particular problem, especially where the donor species is more distantly related, such as donor organs from pigs and sheep to human recipients. Vascular organs present a special difficulty because of hyperacute rejection (HAR).

HAR occurs when the complement cascade in the recipient is initiated by binding of antibodies to donor endothelial cells.

Previous attempts to prevent HAR have focused on two strategies: modifying the immune system of the host by inhibition of systemic complement formation (1,2) and antibody depletion (3,4). Both strategies have been shown to temporarily prolong xenograft survival. However, these methodologies are therapeutically unattractive in that they are clinically impractical and would require chronic immunosuppressive treatments. Therefore, recent efforts to inhibit HAR have focused on genetically modifying the donor xenograft. One such strategy has been to achieve high-level expression of species-restricted human complement inhibitory proteins in vascularized pig organs via transgenic engineering (5–7). This strategy has proven to be useful in that it has resulted in the prolonged survival of porcine tissues following antibody and serum challenge (5,6). Although increased survival of the transgenic tissues was observed, long-term graft survival was not achieved (6). As observed in these experiments and also with systemic complement depletion, organ failure appears to be related to an acute antibody-dependent vasculitis (1,5).

In addition to strategies aimed at blocking complement activation on the vascular endothelial cell surface of the xenograft, recent attention has focused on identification of the predominant xenogeneic epitope recognised by high-titre human natural antibodies. It is now accepted that the terminal galactosyl residue, Gal-α(1,3)-Gal, is the dominant xenogeneic epitope (8–15). This epitope is absent in Old World primates and humans because the α(1,3)-galactosyltransferase (gal-transferase or GT) is non-functional in these species. DNA sequence comparison of the human gene to α(1,3)-galactosyltransferase genes from the mouse (16,17), ox (18), and pig (12) has revealed that the human gene contained two frameshift mutations, resulting in a non-functional pseudogene (20,21). Consequently, humans and Old World primates have pre-existing high-titre antibodies directed at this Gal-α(1,3)-Gal moiety as the dominant xenogeneic epitope.

It appears that different glycosyltransferases can compete for the same substrate. Hence α(1,2)-fucosyltransferase or H transferase (HT) (22) could be an appropriate enzyme to decrease the expression of Gal-α(1,3)-Gal, as both the α(1,2)-fucosyltransferase and the α(1,3)-galactosyltransferase use N-acetyl lactosamine as an acceptor substrate, transferring fucose or galactose to generate fucosylated N-acetyl lactosamine (H substance) or Gal-α(1,3)-Gal, respectively. Furthermore, the α(1,3)-galactosyltransferase of most animals cannot use the fucosylated N-acetyl lactosamine as an acceptor to transfer the terminal galactose, but will only transfer to N-acetyl lactosamine residues (23). We have previously reported that the simultaneous expression of two glycosyltransferases, α(1,2)-fucosyltransferase (H transferase) and α(1,3)-galactosyltransferase, does not lead to equal synthesis of each monosaccharide, but the activity of the α(1,2)-fucosyltransferase is given preference over that of the α(1,3)-galactosyltransferase, so that the expression of Gal-α(1,3)-Gal is almost entirely suppressed (24).

The α(1,3)-galactosyltransferase (Gal transferase) can galactosylate two types of precursor chains: Type 1: Galβ(1,3)GlcNAc and Type 2: Galβ(1,4)GlcNAc.

Furthermore, both of these precursors can be transformed into H substance or fucosylated β-D-Gal by two α(1,2)-fucosyltransferases (25,26). These two fucosyltransferases are H-transferase or FUT1 (22) and secretor (Se) transferase or FUT2 (27). While both enzymes can use both types of precursors, FUT1 HT preferentially utilises Type 2 precursor chains, and FUT2 preferentially utilises Type 1 (28).

In work leading up to the present invention the inventors set out to create a nucleic acid which would be useful in reducing unwanted carbohydrate epitopes on the surface of cells. The nucleic acid could be used in production of an organ which would cause reduced levels of rejection when transplanted into another species. The inventors surprisingly found that a glycosyltransferase derived from porcine origin was useful in decreasing unwanted carbohydrate epitopes in cells. The enzyme encoded by the nucleic acid is able to compete effectively with glycosyltransferases which produce unwanted carbohydrate epitopes. In this particular work the inventors cloned a secretor transferase (Se) gene from pig origin, and demonstrated that this is expressed in cells and results in reduced levels of unwanted epitopes on those cells. The secretor transferase is referred to herein as "pig secretor".

SUMMARY OF THE INVENTION

In a first aspect the invention provides a nucleic acid encoding a first glycosyltransferase which is able to compete with a second glycosyltransferase for a substrate when said nucleic acid is expressed in a cell which produces said second glycosyltransferase, resulting in reduced levels of a product from said second glycosyltransferase.

The nucleic acid may be DNA or RNA, single or double stranded, or covalently closed circular. It will be understood that the nucleic acid encodes a functional gene (or part thereof) which enables a glycosyltransferase with the appropriate activity to be produced. Preferably the nucleic acid is in an isolated form; this means that the nucleic acid is at least partly purified from other nucleic acids or proteins.

Preferably the nucleic acid comprises the correct sequences for expression, more preferably for expression in a eukaryotic cell. The nucleic acid may be present on any suitable vehicle, for example, a eukaryotic expression vector such as pcDNA (Invitrogen). The nucleic acid may also be present on other vehicles, whether suitable for eukaryotes or not, such as plasmids, phages and the like.

Preferably the first glycosyltransferase is a an enzyme with a higher affinity for the substrate than said second glycosyltransferase. More preferably said first glycosyltransferase preferentially utilises Type 1 substrates. Still more preferably said first glycosyltransferase is Se (also known as FUT2). Preferably the Se originates or is derived from, or is based on, Se from the same species as the cell in which it is intended to be expressed. Thus, the first glycosyltransferase and the cell in which the enzyme is expressed may each originate from animals of the same species. Such species may be pig, New World monkey, dog or other suitable species. The nucleic acid encoding Se is not necessarily directly derived from the native gene. The nucleic acid sequence for Se may be made by PCR, constructed de novo or cloned.

More preferably Se is of porcine origin or based on the porcine enzyme. This means that the enzyme is based on, homologous with, or similar to native porcine Se.

More preferably the nucleic acid sequence encoding Se is based on, or similar to a 1.3 kb DNA fragment derived from a pig genomic liver. More preferably the nucleic acid sequence encodes the amino acid sequence shown in FIG. 1 (SEQ. ID. NO: 6). Still more preferably the nucleic acid sequence is that shown in FIG. 1 (SEQ. ID. NO: 5).

It is apparent that the Se gene is not expressed in porcine tissues which are of primary interest for transplantation. Thus Se is not expressed in heart, liver, kidney and pancreas, for example. Thus the invention includes the provision of expression of a gene in a tissue where it is not normally expressed, whereby expression results in reduced levels of unwanted carbohydrate epitopes in that tissue and renders an organ composed of that tissue more suitable for transplantation.

The second glycosyltransferase may be any enzyme which produces an unwanted carbohydrate epitope on the cell of interest. This will usually be Gal transferase.

Preferably the cell which expresses the nucleic acid of the invention is a eukaryotic cell. More preferably it is a mammalian cell, still more preferably a New World monkey cell, even more preferably an ungulate cell (pig, sheep, goat, cow, horse, deer, camel, etc.) or a cell from other species such as dogs. Still more preferably the cell is a pig cell.

In a related aspect the invention provides a nucleic acid encoding a first glycosyltransferase which is able to compete with a second glycosyltransferase when said nucleic acid is expressed in a cell which produces said second glycosyltransferase, wherein said first glycosyltransferase is able to utilise more than one substrate, resulting in reduced levels of product from said second glycosyltransferase.

The greater substrate specificity of the first glycosyltransferase means that this enzyme is more efficient at converting substrate to the desired carbohydrate and more effective in reducing the ability of the second glycosyltransferase to produce unwanted carbohydrate epitopes.

Preferably the first glycosyltransferase is Se, still more preferably the Se is as described above.

Still more preferably the first glycosyltransferase has a higher affinity for one or more of its substrates than the second glycosyltransferase.

The invention also extends to isolated proteins produced by the nucleic acid of the invention. It further extends to biologically or functionally active fragments of such proteins.

In another aspect the invention provides a method of producing a nucleic acid encoding a first glycosyltransferase which is able to compete with a second glycosyltransferase for a substrate when said nucleic acid is expressed in a cell which produces said second glycosyltransferase, resulting in reduced levels of product from said second glycosyltgransferase, said method comprising operably linking a nucleic acid sequence encoding a first glycosyltransferase to an appropriate vector or other nucleic acid in order to obtain expression of said first glycosyltransferase.

Those skilled in the art will be aware of the techniques for producing the nucleic acid. Standard techniques such as those described in Sambrook et al may be employed.

Preferably the nucleic acid sequences are the preferred sequences described above.

In another aspect the invention provides a method of reducing the level of a carbohydrate exhibited on the surface of a cell, said method comprising the step of causing a nucleic acid to be expressed in said cell wherein said nucleic acid encodes a first glycosyltransferase which is able to compete for substrate with a second glycosyltransferase and wherein said cell produces said second glycosyltransferase which is capable of producing said carbohydrate.

The cell may be any suitable cell, preferably those described above.

The invention also extends to cells produced by the above method and organs comprising the cells.

The nucleic acid of the invention may be present in the cell with another nucleic acid construct which also downregulates production of unwanted carbohydrates in the surface of the cells, such as that disclosed in PCT/US95/07554, or that of an International application based on Australian provisional application PO1402 filed Aug. 2, 1996 in the name of The Austin Research Institute.

In another aspect the invention provides a method of producing a cell from one species, such as a donor, which cell is immunologically acceptable to another species which is a recipient, comprising the step of reducing levels of carbohydrate on said cell which cause it to be recognised as non-self by the recipient species, said method comprising causing a nucleic acid to be expressed in said cell, wherein said nucleic acid encodes a first glycosyltransferase which is able to compete for a substrate with a second glycosyltransferase and wherein said cell produces said second glycosyltransferase which is capable of producing said carbohydrate.

The cell may be from any of the species mentioned above. Preferably the cell is from a New World primate or a pig. More preferably the cell is from a pig.

The invention also extends to non-human transgenic animals comprising or harbouring the nucleic acid of the invention.

In another aspect the invention provides an expression unit such as a retroviral packaging cell or retroviral packaging cassette, a retroviral construct or a retroviral producer cell which expresses the nucleic acid of the invention, resulting in a cell which is immunologically acceptable to an animal by having reduced levels of a carbohydrate on its surface, which carbohydrate is recognised as non-self by said animal.

Preferably the animal is a human, ape or Old World monkey.

The retroviral packaging cells or retroviral producer cells may be cells of any animal origin in which it is desired to reduce the level of carbohydrates on the cell surface to make it more immunologically acceptable to a host. Such cells may be derived from mammals such as canine species, rodent or ruminant species and the like.

The invention also extends to a method of producing a retroviral packaging cell or a retroviral producer cell having reduced levels of a carbohydrate on its surface, wherein the carbohydrate is recognised as non-self by an animal, comprising transforming/transfecting the retroviral packaging cell or the retroviral producer cell with the nucleic acid of the invention under conditions such that the chimeric enzyme is produced. The "chimeric enzyme" means the enzyme encoded by the nucleic acid of the invention.

The term "nucleic acid" refers to any nucleic acid comprising natural or synthetic purines and pyrimidines.

The terms "originates", "based on", or "derived from" mean that enzyme is homologous to, or similar to, the enzyme from that species.

The term "glycosyltransferase" refers to a polypeptide with an ability to move carbohydrates from one molecule to another.

The term "operably linking" means that the nucleic acid sequences are ligated such that a functional protein is able to be transcribed and translated.

The term "reducing the level of a carbohydrate" refers to lowering, minimising, or in some cases, ablating the amount of carbohydrate displayed on the surface of the cell. Preferably said carbohydrate is in the absence of the first glycosyltransferase of the invention, capable of stimulating recognition of the cell as "non-self" by the immune system of an animal. The reduction of such a carbohydrate therefore renders the cell, or an organ composed of said cells, more acceptable to the immune system of an animal in a transplant situation or gene therapy situation.

The term "causing a nucleic acid to be expressed" means that the nucleic acid is introduced into the cell (i.e. by transformation/transfection or other suitable means) and contains appropriate signals to allow expression in the cell.

The term "immunologically acceptable" refers to producing a cell, or an organ made up of numbers of the cell, which does not cause the same degree of immunological reaction in the other species as a native cell from the one species. Thus the cell may cause a lessened immunological reaction, only requiring low levels of immunosuppression therapy to maintain such a transplanted organ or no immunosuppression therapy may be necessary.

It is contemplated that the nucleic acid of the invention may be useful in producing the chimeric nucleic acids disclosed in an application based on Australian provisional application PO1402 filed Aug. 2, 1996 in the name of The Austin Research Institute.

The retroviral packaging cell and/or producer cells may be used in applications such as gene therapy. General methods involving use of such cells are described in PCT/US95/07554 and the references discussed therein.

DETAILED DESCRIPTION OF THE INVENTION

The invention will now be described by way of reference only to the following non-limiting figures and example.

FIG. 1 shows the nucleic acid sequence (SEQ. ID. NO: 5) and corresponding amino acid sequence (SEQ. ID. NO:6) of a porcine secretor sequence.

Figure 2:
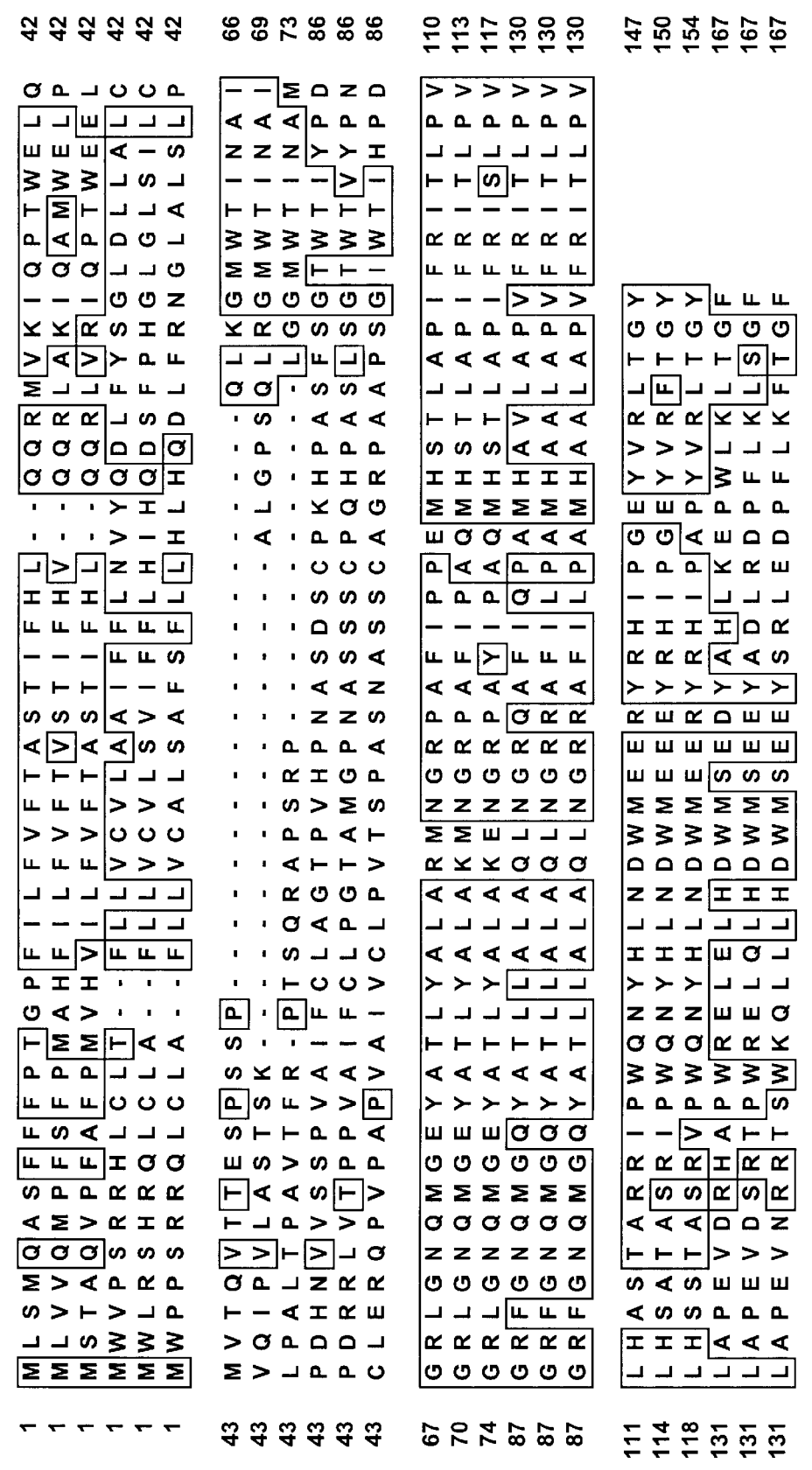
Figure 2:
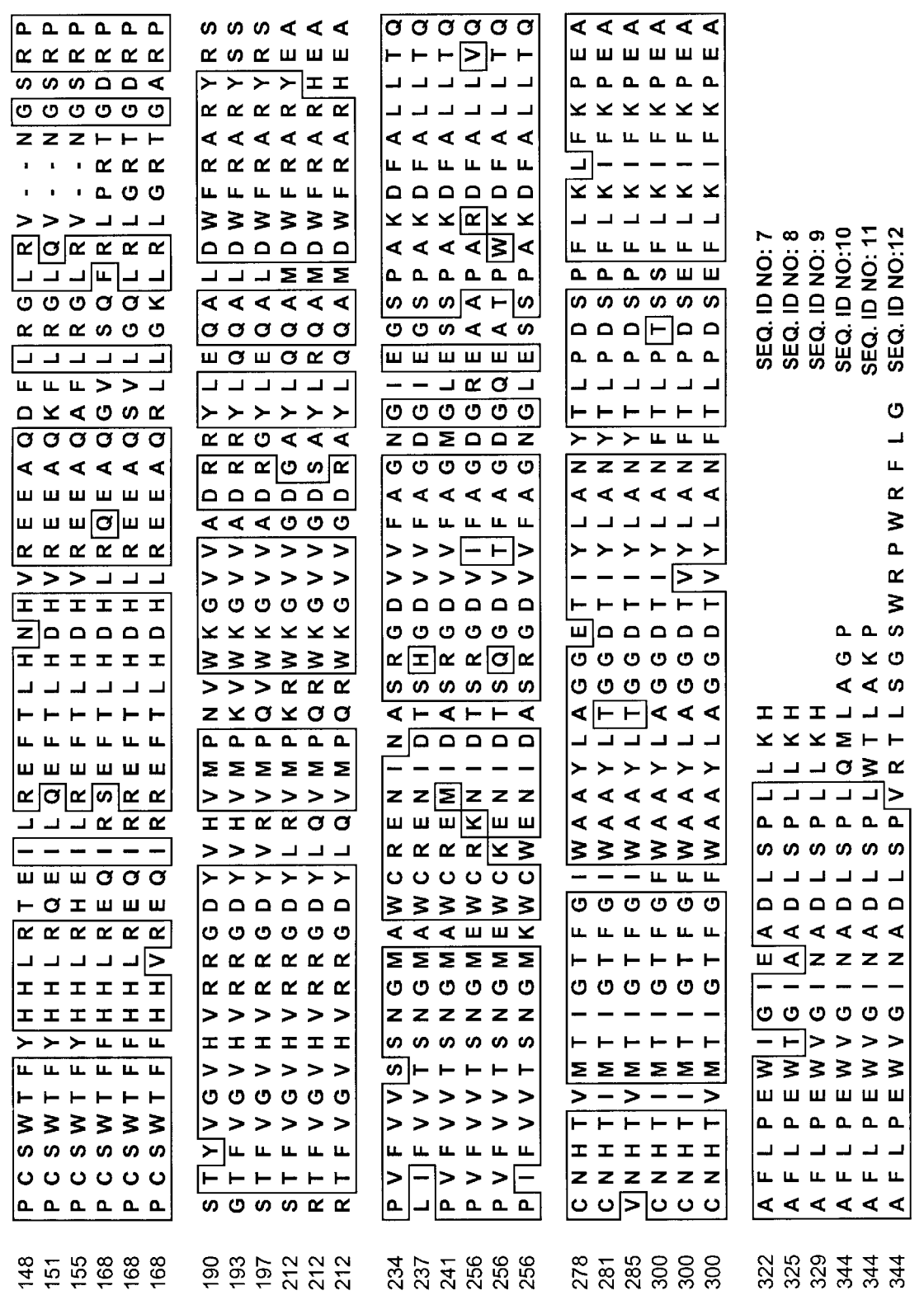

FIG. 2 shows a comparison of the amino acid sequences of pig, human and rabbit FUT1 and FUT2. The rows in each panel represent pig (SEQ. ID. NO: 7), human (SEQ. ID. NO: 8) and rabbit (SEQ. ID. NO: 9) FUT2 and pig (SEQ. ID. NO: 10), human (SEQ. ID. NO: 11) and rabbit (SEQ. ID. NO: 12) FUT1 from top to bottom.

Figure 3:
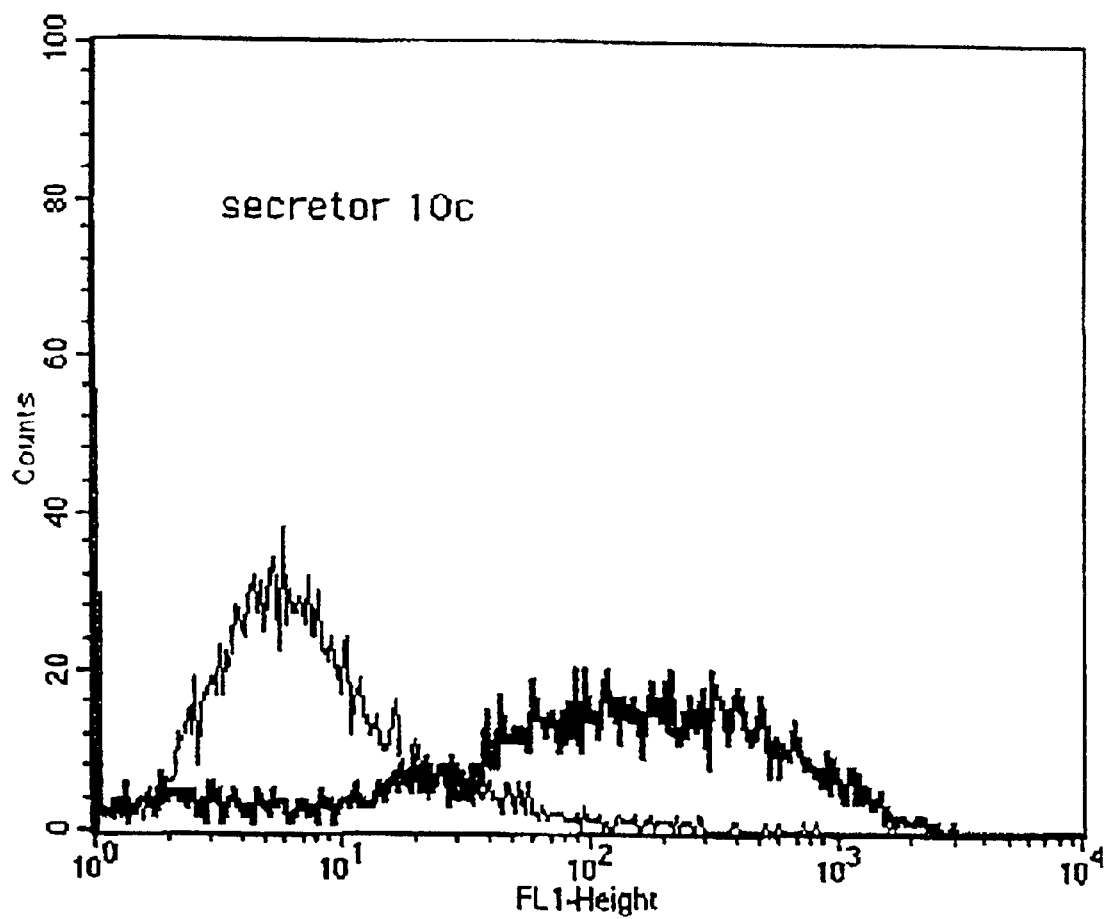
FIG. 3 shows a typical FACS profile of pig endothelial cells which express α(1,2)-fucosyltransferase.

The work presented below is surprising in that the inventors had previously attempted to clone human secretor but were unsuccessful. A non-functional human pseudogene for secretor was cloned. This raised the question of whether other species such as pigs have a functional gene for secretor. The fact that the inventors were able to successfully clone the pig secretor gene and use it to down regulate unwanted epitopes was surprising. Because of the differences in blood group antigens between pigs and humans, it was not known whether pigs have secretor antigens. The cloning of a functional gene indicates that pigs do have the epitope produced by the secretor glue.

Furthermore, although FUT1 had been cloned, it did not permit the pig secretor gene to be isolated. FUT1 and FUT2 are sufficiently different in that probes based on the sequence of FUT1 do not hybridise with that of FUT2.

EXAMPLE 1

Cloning of Pig Secretor

Cloning

The gene encoding the sequence for the human secretor gene (Sec2) (27) was cloned from human genomic DNA using a PCR strategy according to the published sequence, primers, and conditions. A pig genomic liver library in EMBL-3 (Clonetech Laboratories, Palo Alto, Calif.) was screened using this human clone. Nine clones were obtained after screening $5 \times 10^5$ plaques. Two of these were randomly chosen for further examination. Limited restriction mapping showed identical banding patterns for both clones, with a 3.3 kb PstI fragment specifically hybridising with the human (Sec 2 α(1,2)-fucosyltransferase) probe. This fragment (PSe 16.1) was sequenced using the ABI automated sequencer.

For functional studies the coding segment of the genomic clone was subcloned into an expression vector. Utilising the polymerase chain reaction (PCR), and the Pig Se sequence as obtained above, 1048 bp gene product was derived using primers: 5' primer homologous to the 5' UTR: 5' CAG AGACTTATGCTCAGCATGCAGGC (SEQ. ID. NO: 1) in which the underlined sequence contains a unique Hind III site; 3' primer homologous to the 3'UTR: 5'-5'-GTC CTGCAGTGAGTGCTTAAGGAGTGG (SEQ. ID. NO: 2) where the underlined sequence contains a PstI site. This PCR product was purified as above, digested with HindII and PstI, ligated with similarly digested pcCNA (Invitrogen Corporation, San Diego, Calif.), and then used to transform MC1061/P3. One clone, designated pPSet, which encodes the cDNA for the porcine α(1,3)-galactosyltransferase (19), and pPHT, which encodes the cDNA for the porcine "H" α:(1,2)-fucosyltransferase (33).

Transfection

COS cells were maintained in Dulbecco's modified Eagles Medium (DMEM) (Cytosystems Pty. Ltd., Castle Hill, NSW, Australia). COS cells were transfected using the DEAE-dextran method, using DMEM medium supplemented with Foetal Clone II(Hy clone Utah), and 48 h later cells were examined for cell surface expression.

Serology

Direct fluorescence stainey of cell surface carbohydrate epitopes was performed with FITC or TRITC conjugated lectins: IB4 lectin isolated from *Griffonia simplicifolia* (Sigma, St. Louis, Mo.) detects Gal-α(1,3)-Gal and UEAI lectin isolated from *Ulex europaeus* (Sigma, and EY Laboratories, Inc., San Mateo, Calif.) detects H substance. H substance was also detected by indirect immunofluorescence using a monoclonal antibody (mAb) specific for the H-epitope (ASH-1952) developed at the ARI, and FITC conjugated goat anti-mouse IgG (Zymed Laboratories, San Francisco, Calif.) used to detect murine antibody binding.

Enzyme Assays

Cells were washed twice with phosphate buffered saline and lysed in either 1% Triton X100/100 mM Tris pH7.0 or 1% Triton X100/100 mM sodium cacodylate pH 6.5/25 mM $MnCl_2$ at 4° C. for 30 min, lysates centrifuged and the supernatant collected and stored at −70° C. Protein concentration was determined by the Bradford method, using bovine serum albumin as a standard; 5–20 μg of cell extract was used per transferase assay. The assay for α-1,2 fucosyltransferase involved mixing cell extracts and acceptor (75 mM pheny-β-Dgalactoside (Sigma)) in 50 μl 50 mM MOPS (3-[N-Morpholino]propanesulphonic acid) pH 6.5; 20 mM $MnCl_2$; 5 mM ATP; 3 μM GDP[$^{14}$C]-Fuc (specific activity 287 mCi/mmol, Amersham International plc, Amersham, UK) and incubation for 2 h at 37° C. The reaction was terminated by the addition of ethanol, and the incorporated $^{14}$C-Fuc determined by liquid scintillation counting after separation in Sep-Pak C18 cartridges (Waters-Millipore, Millford, Mass.). In all cases the parallel reactions were performed in the absence of added acceptor molecules, to allow for the calculation of specific incorporation.

Results

Cloning of Pig FUT2 (Se)

Two clones were obtained after screening 5×10$^5$ plaques of a pig genomic liver library in EMBL-3 (Clonetech Laboratories, Palo Alto, Calif.) with the cDNA fragment encoding the full length human FUT2 (27). Limited restriction mapping showed identical banding patterns for both clones, with a 3.3 kb Pst I fragment specifically hybridising with the human FUT2 probe. This fragment was subcloned to generate the clone pSel6.1, which was sequenced. The complete nucleotide sequence of the pig FUT2 DNA contains 1269 bp of nucleotide sequence (FIG. 1): a 8 bp 5' untranslated (UT) region, an open reading frame of 1060 bp encoding a 340 amino acid protein with the initiation codon being nucleotide 9, succeeded by 156 bp of 3' UT. The predicted protein sequence of the pig FUT2 suggests a type II integral membrane protein, typical of other glycosyltransferases. There are three distinct structural features of the predicted protein: (i) a short (4 amino acid) amino-terminal cytoplasmic tail; (ii) a putative transmembrane region composed of 21 hydrophobic amino acids (residues 5–26), flanked on either side by charged amino acid residues; (iii) a 314 amino acid carboxyl-terminal domain which contains three potential N-linked glycosylation sites.

Comparison of the amino acid sequences of pig FUT2 with the human (22,27) and rabbit (29) α(1,2)-fucosyltransferases shows the highest identity with the Se transferase rather than the H transferase (FIG. 2): the pig FUT2 shows 83.2% identity with human FUT2, 74.1% identity with rabbit FUT2, 58.5% identity with pig FUT1, 57.1% identity with human FUT1, and 58.8% identity with rabbit FUT1. We note that the highest sequence identity is in the carboxyl portion of the molecule, which contains the catalytic domain (30).

The pig FUT2 nucleotide sequence shows about 36% homology with human FUT1.

Expression of H Substance After Transfection With Pig FUT2

The 1.3 kb Pst I fragment containing the coding sequence was subcloned into the COS cell expression vector pCDNA-1 (Invitrogen Corporation San Diego, Calif.). COS cells transfected with the cloned genomic DNA encoding the pig FUT2 expressed H substance, as indicated by staining with fluoresceinated UEA I lectin, which detects H substance (31) (~65% positive as shown in Table 1). After transfection with the pig FUT1 CDNA clone similar staining was observed while no staining was seen with the reagent on COS cells transfected with the CDNA for the pig α(1,3)-galactosyltransferase (19). In contrast, staining with fluoresceinated IB4 lectin, which detects Galα(1,3)Gal (32), was detected on COS cells transfected with pig α(1,3)-galactosyltransferase cDNA but not with the pig FUT1 or FUT2 DNA.

TABLE 1

Cell surface staining of transfected COS cells.

| Transfection with cDNA encoding[1] | | | % Staining | |
|---|---|---|---|---|
| FUT1 | FUT2 | GT | UEA1 | IB4 |
| + | − | − | 75 | 0 |
| − | + | − | 68 | 0 |
| − | − | + | 0 | 65 |
| + | − | + | 72 | 8 |
| − | + | + | 73 | 9 |
| + | + | + | 76 | <1 |

[1]cDNA encoding pig FUT1, FUT2 and GT used

Enzymatic Studies

Cell lysates prepared from COS cells transfected with pFUT2 and pFUT1 were assayed for α(1,2)-fucosyltransferase activity. Using mock-transfected COS cells to show baseline activity (1.1 nmol hr$^{-1}$ mg$^{-1}$), significant α(1,2)-fucosyltransferase activity was observed in lysates from both pFUT2 (151.1 nmol hr$^{-1}$ mg$^{-1}$) and pFUT1 (140.0 nmol hr$^{-1}$ mg$^{-1}$) transfected COS cells, but not in ppGT transfected COS cells (6.7 nmol hr$^{-1}$ mg$^{-1}$). The enzyme activity measured in these lysates reflects the expression of H substance on the cell surface as shown in Example 2.

Cotransfection of COS Cells

COS cells transfected with the pig α(1,3)-galactosyltransferase cDNA clone expressed Gal-α(1,3)-Gal as indicated by reactivity with the IB4 lectin (65% of cells reactive) (Table 1). COS cells was also able to express H substance, as after transfection with either the pig FUT2 or FUT1 clones they stained with the UEAI lectin (68 and 75% of cells respectively reactive, Table 1). However, when the COS cells were simultaneously transfected with the pig α(1,3)-galactosyltransferase cDNA clone and either pig FUT2 or pig FUT1, and examined for cell surface staining of either carbohydrate, the cells predominantly expressed H substance (72% of cells positive, Table 1), compared with 8% of cells expressing Galα(1,3)-Gal (Table 1). When both pig FUT2 and pig FUT1 were cotransfected together with the pig α(1,3)-galactosyltransferase cDNA, only one H substance was detected (76%) and <1% Galα(1,3)-Gal (Table 1). This reduction observed using FUT1 and FUT2 was specific and not due to amount of DNA used for transfection, because using twice the amount of DNA for either FUT1 or FUT2 alone had no effect on the expression of Galα(1,3)-Gal. Thus expression of both FUT2 and FUT1 resulted in a major decrease in expression of Galα(1,3)-Gal.

EXAMPLE 2

Enzyme Kinetics

Cell lysates prepared from COS cells transfected in the manner described in Example 1 with pFUT2 (pig Se), pFUT1 (pig H transferase), or with vector alone were assayed for α(1,2)-fucosyltransferase activity, and the kinetic values were calculated. The Km values (reflecting the affinity for substrate) obtained for pFUT1, and pFUT2 are shown in Table 2. These values were compatible with those of human and rabbit homologues that have been reported.

The respective Km values obtained for pFUT1, and pFUT2 with various substrates were:

(a) Galβ(1,3)GlcNAc (Type I): 6.0 mM for pFUT1 and 1.3 mM for pFUT2.

The Km values reported for rabbit FUT1 and rabbit FUT2 were 3.1 mM and 1.5 mM respectively (34) and 2 mM and 1 mM for human FUT1 and human FUT2 respectively (35).

(b) Galβ(1,4)GlcNAc (Type II): 3.7 mM for pFUT1 and 4.4 mM for pFUT2.

The Km values reported for rabbit FUT1 and rabbit FUT2 were 4.2 mM and 6.7 mM respectively (34) and 1.9 mM and 5.7 mM for human FUT1 and human FUT2 respectively (37).

(c) Galβ(1,3)GalNAc (Type III): 14 mM for pFUT1 and for pFUT2 0.2 mM.

The Km values reported for rabbit FUT1, and rabbit FUT2 were 5.8 mM and 1 mM respectively (34).

(d) Galβ(1,4)Gal: 4.2 mM and 1.5 mM for pFUT1 and pFUT2 respectively.

(e) Galβ(1,4)Glc, 1.9 mM and 7.4 mM for pFUT1 and pFUT2 respectively.

Thus, pFUT1 can be distinguished from pFUT2 on the basis of substrate preference; pFUT1 is relatively specific for type II and type IV substrates, while pFUT2 (and other Secretor homologues), although having greater affinity for type I and III acceptors, will use other substrates.

TABLE 2

Enzyme Kinetics of pFUT1 and pFUT2
Apparent Km of pig α(1,2)-fucosyltransferases,
pFUT1 (H type) and pFUT2 (Secretor type), obtained with various substrates.

| Substrate | | pFUT1 | pFUT2 |
| --- | --- | --- | --- |
| | | (Km in mM) | |
| Type I | Galβ(1,3)GlcNAc | 6.0 | 1.3 |
| Type II | Galβ(1,4)GlcNAc | 3.7 | 4.4 |
| Type III | Galβ(1,3)GalNAc | 14 | 0.2 |
| Type IV | Galβ(1,4)Gal | 4.2 | 1.5 |
| Lactose | Galβ(1,4)Glc | 1.9 | 7.4 |

EXAMPLE 3

Generation of Pig Endothelial Cells Expressing Chimeric α(1,2)-fucosyltransferase The pig endothelial cell line PIEC expressing the Secretor type α(1,2)-fucosyltransferase were produced by lipofectamine transfection of pFUT2 plasmid DNA (20 μg) and pSV2NEO (2 μg). Cells with stable integration were selected by growing the transfected PIEC in media containing G418 (500 ug/ml; Gibco-BRL, Gaithersburg, Md.).

Fourteen independant clones were examined for cell surface expression of H substance by staining with UEA-1 lectin. >95% of cells of each of these clones were found to be positive: FIG. 3 shows a typical FACS profile obtained for these clones.

EXAMPLE 4

Production of the Transgenic Construct, Purification, and Microinjection.

A 1023 bp NruI/NotI DNA fragment, encoding the full length pFUT2 was generated utilizing the Polymerase Chain Reaction and the phHT plasmid (36) using the primers:

5' primer homologous to the 5' UTR:

5'-CAT<u>GCGGCCGC</u>TCAGTGCTTAAGGAGTGGGGAC-3' (SEQ. ID. NO: 3)

The underlined sequence contains a unique NruI site;
3' primer homologous to the 3'UTR:

5'-GAG<u>TCGCGA</u>ATGCTCAGCATGCAGGCATCTTTC-3' (SEQ. ID. NO: 4)

The DNA was purified on gels before being electroeluted and subcloned into a NruI/NotI cut genomic H-2K$^b$ containing vector (38), resulting in the plasmid clone (pH-2K$^b$-pFUT2) encoding the pFUT2 gene directionally cloned into exon 1 of the murine H-2K$^b$ gene. This produced a transcript that commences at the H-2K$^b$ transcriptional start site, continuing through the pFUT2 cDNA insert. The construct was engineered such that translation would begin at the initiation codon (ATG) of the pFUT2 CDNA and terminate at the stop codon (TGA) 1023 bp downstream.

DNA was prepared for microinjection by digesting pH-2K$^b$-pFUT2 with XhoI and purification of the H-2K$^b$-pFUT2 DNA from the vector by electrophoretic separation in agarose gels, followed by extraction with chloroform, and precipitation in ethanol to decontaminate the DNA. Infections were performed on the pronuclear membrane of (C57BL/6×SJL)F$_1$ zygotes at concentrations between 2–5 ng/μl, and the zygotes were then transferred to pseudopregnant (C57BL/6×SJL)F$_1$ females.

Screening for the Transgene

Figure 4:
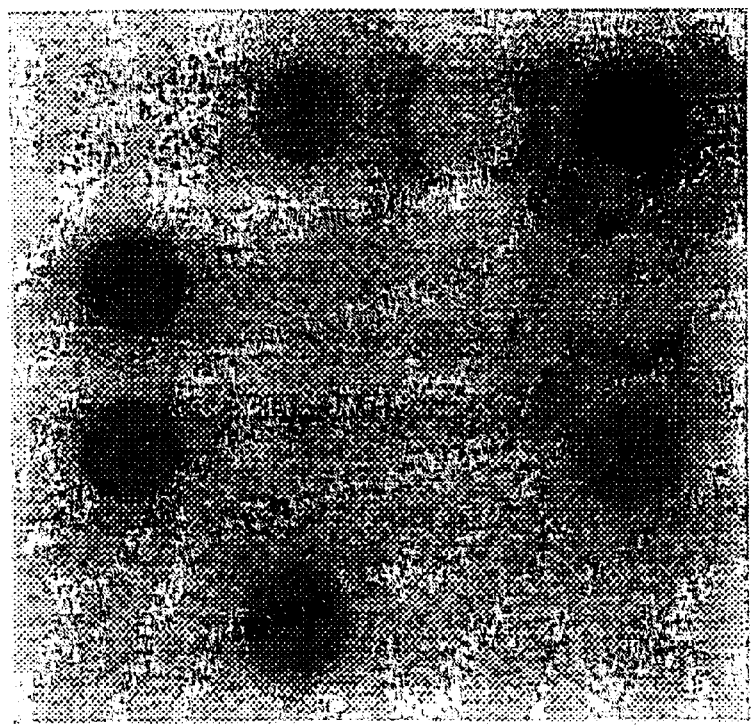
FIG. 4 is a dot blot showing the presence of α(1,2)-fucosyltransferase in six offspring of mice injected with a transgenic construct.

The presence of the transgene in live offspring was detected by dot blotting. 5 μg of genomic DNA was transferred to nylon filters and hybridized with the insert from pFUT2, using a final wash comprising 0.1×SSC/1% SDS at 68° C. FIG. 4 shows the results of testing 16 live offspring, of which six were found to have the transgenic construct integrated into the genome. Expression of transgenic protein is examined by haemagglutination and fucosyltransferase activity.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

1. Leventhal, J R et al. Complement depletion prolongs discordant cardiac xenograft survival in rodents and non-human primates. Transplantion Proc. 25, 398–399 (1993).
2. Pruitt, S et al. The effect of soluble complement receptor type 1 on hyperacute rejection of porcine xenografts. Transplantation 57, 363–370 (1994).
3. Leventhal, J R et al. Removal of baboon and human. antiporcine IgG and IgM natural antibodies by immunoabsorption. Transplantation 59, 294–300 (1995).
4. Brewer, R J et al. Depletion of preformed natural antibody in primates for discordant xenotransplantation by continuous donor organ plasma perfusion. Transplantation Proc. 25, 385–386 (1993).

5. McCurry, K R et al. Human complement regulatory proteins protect swine-to-primate cardiac xenografts from humoral injury. Nature Med. 1, 423–427 (1995).
6. Fodor, W L et al. Expression of a functional human complement inhibitor in a transgenic pig as a model for the prevention of xenogeneic hyperacute organ rejection. Proc. Natl. Acad. Sci USA 91, 11153–11157 (1994).
7. Rosengard, A M et al. Tissue expression of the human complement inhibitor decay accelerating factor in transgenic pigs. Transplantation 59, 1325–1333 (1995).
8. Sandrin, M S, Vaughan, H A, Dabkowski, P L & McKenzie, I F C. Anti-pig IgM antibodies in human serum reacts predominantly with Gal($\alpha$1,3)Gal epitopes. Proc. Natl. Acad. Sci USA 90, 11391–11395 (1993).
9. Sandrin, M S, Vaughan, H A & McKenzie, I F C. Identification of Gal($\alpha$1,3)Gal as the major epitope of pig-to-human vascularised xenografts. Transplantation Rev. 8, 134–149 (1994).
10. Sandrin, M S & McKenzie, I F C. Gal($\alpha$1,3)Gal, the major xenoantigen(s) recognised in pigs by human natural antibodies. Immunol. Rev. 141. 169–190 (1994).
11. Cooper, D K C et al. Identification of $\alpha$-galactosyl and other carbohydrate epitopes that are bound by human anti-pig antibodies. Relevance to discordant xenografting in man. Transplantation Immun. 1. 198–205 (1993).
12. Cooper, D K C, Koren, E & Oriol, R. Oligosaccharides and discordant xenotransplantation. Immunol. Rev. 141. 31–58 (1994).
13. Good, A H et al. Identification of carbohydrate structures that bind antiporcine antibodies: Implications for discordant xenografting in humans. Transplantation Proc. 24. 559–562 (1992).
14. Galili, U., Clark, M R., Shohet, S B., Buehler, J & Macher, B A. Evolutionary relationship between the natural anti-Gal antibody and the Gal$\alpha$1–3Gal epitope in primates. Proc. Natl. Acad. Sci USA 84. 1369–1373 (1987).
15. Galili, U., Shohet, S B., Korbin, E., Stults, C L M & Macher, B A. Man, apes and old world monkeys differ from other mammals in the expression of the $\alpha$-galactosyl epitopes on nucleated cells. J. Biol. Chem. 263. 17755–17762 (1988).
16. Larsen, R D et al. Isolation of a cDNA encoding a murine UDPgalactose: $\beta$-D-galactosyl-1, 4-N-acetyl-glucosaminide-1,3-galactosyltransferase: Expression cloning by gene transfer. Proc. Natl. Acd. Sci. USA 86. 8227–8231 (1989).
17. Joziasse, D H., Shaper, J H., Kim D., Van den Eijnden, D H & Shaper, J H. Murine $\alpha$1,3 galactosyltransferase a single gene locus specifies four isoforms of the enzyme by alternative splicing. J. Biol. Chem. 267, 5534–5541 (1992).
18. Joziasse, D H, Shaper, J H, Van den Eijnden, D H, Van Tunen, A J & Shaper, N L. bovine $\alpha$1,3 galactosyltransferase: Isolation and characterisation of a cDNA cone. Identification of homologous sequences in human genomic DNA. J. Biol, Chem. 264. 14290–14297 (1989).
19. Sandrin, M S, Dabkowski, P I, Henning, M M, Mouhtouris, E & McKenzie, I F C. Characterization of CDNA clones for porcine $\alpha$1,3 galactosyltransferase. The enzyme generating the Gal($\alpha$1,3)Gal epitope. Xenotransplantation 1, 81–88 (1994).
20. Joziasse, D H, Shaper, J H, Jabs, F W & Shaper, N L. Characterization of an $\alpha$1,3-galactosyltransferase homologue on human chromosome 12 that is organised as a processed pseudogene. J. Biol. Chem. 266. 6991–6998 (1991).
21. Larsen, R D, Rivera-Marrero, C A, Ernst, L X, Cummings, R D & Lowe, J B. Frameshift and non sense mutations in a human genomic sequence homologous to a murine a UDP-Gal: $\beta$-D-Gal 1,4-D-GlcNAc$\alpha$1,3-galactosyltransferase cDNA. J. Biol. Chem. 265. 7055–7061 (1990).
22. Larsen, R. D., L. K. Ernst, R. P. Nair, and J. B. Lowe. 1990. Molecular cloning, sequence, and expression of a human GDP-L-fucose: $\beta$-D-galactoside 2-$\alpha$-L-fucosyltransferase cDNA that can form the H blood group antigen. Proc. Natl. Acad. Sci. USA 87:6674.
23. Blanken, W. M., and D. H. Van den Eijnden. 1985. Biosynthesis of terminal Gal$\alpha$1→3Gal$\beta$1→4GlcNAc-R oligosaccharide sequences on glycoconjugates. Purification and acceptor specificities of a UDP-Gal:N-acetyllactosamine $\alpha$1→3galactosyltransferase from calf thymus. J. Biol. Chem. 260:12927.
24. Sandrin, M. S., Fodor, W. L., Mouhtouris, E., Osman, N., Cohney, S., Rollins, S. A., Guilmette, E. R., Setter, E., Squinto, S. P., and McKenzie, I. F. C.1995. Enzymatic remodeling of the carbohydrate surface of a xenogenic cell substantially reduces human antibody binding and complement-mediated cytolysis. Nature Medicine 1: 1261.
25. Hakemori, S.: Immunochemical and molecular genetic basis of the histo-blood group ABO(H) and related antigen system. Baillére's Clinical Haematology 4: 957–974, 1991
26. Lowe, J. B.: The blood group-specific human glycosyltransferases. Baillére's Clinical Haematology 6: 465–492, 1993
27. Kelly, R. J., Rouguier, S., Giorgi, D., Lennon, G. G., and Lowe, J. B.: Sequence and expression of a candidate for the human Secretor blood group $\alpha$(1,2)-fucosyltransferase gene (FUT2). Homozygosity foe an enzyme-inactivating nonsense mutation commonly correlates with the non-secretor phenotype. J. Biol Chem 270: 4640–4649, 1995
28. Oriol, R., Mollicone, R., Coullin, P., Dalix, A-M., and Candelier, J-J. Genetic regulation of the expression of ABH and Lewis antigens in tissues. APMIS suppl. 27, Vol 100:28–38, 1992.
29. Hitoshi, S., Kusunoki, S., Kianazawa, I., and Tsuji, S. : Molecular cloning and expression of two types of rabbit $\beta$-galactoside $\alpha$1,2-fucosyltransferase. J. Biol Chem 270: 8844–8850, 1995.
30. Joziasse, D. H. Mammalian glycosyltransferases genomic organisation and protein structure. Glycobiology 2: 271–277, 1992.
31. Matsumoto, I. and Osawa, T.: Purification and characterization of an anti-H(O) phytohemagglutinin of Ulex europeus. Biochim Biophys Acta 194: 180–189, 1969
32. Hayes, C. E. and Goldstein, I. J.: An $\alpha$-D-galactosyl-binding lectin from Bandeiraea simplicifolia seeds. J. Biol Chem 249: 1904–1914, 1974
33. Cohney, S., Mouhtouris, E., McKenzie, I.F.C. and Sandrin, M. S.: Molecular cloning of a pig $\alpha$1,2 fucosyltransferase. Immunogenetics 44: 76–79 (1996).
34. Hitoshi, S., Kusunoki, S., Kanazawa, I., and Tsuji, S. Molecular cloning and expression of a third type of rabbit GDP-L- fucose:beta-D-galactoside 2-alpha-L-fucosyltransferase. J Biol Chem 271, 16975–16981 (1996).
35. Le Pendu, J., Cartron, J. P., Lemieux, R. U., and R., O. The presence of at least two different H-blood-group related $\beta$-D-Gal $\alpha$-2-Lfucosyltransferases in human serum and the genetics of blood group H substances. Am. J. hum. Genet. 37, 749–760 (1985).

36. Sandrin, M. S., Fodor, W. L., Mouhtouris, E., Osman, N., Cohney, S., Rollins, S. A., Guilmette, E. R., Setter, E., Squinto, S. P., and McKenzie, I. F. C. Enzymatic remodeling of the carbohydrate surface of a xenogenic cell substantially reduces human antibody binding and complement-mediated cytolysis. Nature Medicine 1, 1261–1267 (1995).

37. Sarnesto, A., Kohlin, T., Hindsgaul, O., Thurin, J., and Blaszczyk-Thurin, M. Purification of the secretor-type beta-galactoside alpha 1-2-fucosyltransferase from human serum. J Biol Chem 267, 2737–2744 (1992).

38. Weiss, E. H., Golden, L., Zakut, R., Mellor, A., Fahrner, K., Kvist, S., and Flavell, R. A. The DNA sequence of the H-2Kb gene: evidence for gene conversion as a mechanism for the generation of polymorphism in histocompatibility antigens. EMBO J 2, 453–462 (1983).

What is claimed is:

1. An isolated nucleic acid encoding the amino acid sequence shown in FIG. 1. (SEQ. I.D. No. 6).

2. The nucleic acid according to claim 1, comprising the sequence shown in FIG. 1. (SEQ. I.D. No.5).

3. A nucleic acid encoding:
   a first porcine Se glycosyltransferase comprising SEQ ID No.6 that:
   i) catalyses transfer of a fucosyl residue to a Galβ(1, 3)GlcNac acceptor substrate, and
   ii) has a higher affinity for said acceptor substrate, as measured by Km, relative to a second glycosyltransferase that shares said acceptor substrate therewith,
   such that when the porcine Se glycosyltransferase is expressed in a cell compartment in which the second glycosyltransferase is present, the porcine Se glycosyltransferase utilizes said acceptor substrate thereby resulting in reduced levels of a product of an action of said second glycosyltransferase on said acceptor substrate, when compared with the level of said product in a cell wherein the porcine Se glycosyltransferase is not expressed.

4. The nucleic acid according to claim 3, wherein the second glycosyltransferase is Gal transferase.

5. The nucleic acid according to claim 3, where the cell is from a mammal selected from the group consisting of primates, ungulates, and dogs.

6. The nucleic acid according to claim 5, wherein the mammal is a pig.

7. The nucleic acid according to claim 3, wherein said porcine Se glycosyltransferase is further able to catalyze transfer of a fucosyl residue to a Galβ(1,4) Glc Nac acceptor substrate.

8. A vehicle comprising the nucleic acid according to claim 3, selected from the group consisting of a pcDNA-1, a plasmid and phage.

9. The vehicle according to claim 8, which enables said nucleic acid to be expressed in prokaryotes or in eukaryotes.

10. An isolated protein or catalytically active fragment thereof, the protein or catalytically active fragment thereof being produced upon expression of the nucleic acid of claim 3.

11. An isolated cell comprising a nucleic acid according to claim 3.

12. An expression unit comprising the nucleic acid of claim 3, selected from the group consisting of a retroviral particle, a retroviral construct and a retroviral producer cell.

13. A method of producing an isolated cell having reduced levels of Galα(1,3)-Gal epitope on the cell surface wherein the carbohydrate epitope is recognized as non-self by a human, comprising the step of transforming or transfecting said cell with the nucleic acid according to claim 3, under conditions such that the porcine Se glycosyltransferase encoded by SEQ ID No. 6 is produced.

14. The nucleic acid according to claim 3, wherein the second glycosyltransferase comprises α(1,3) galactosyltransferase.

15. A nucleic acid according to claim 3, comprising SEQ. I.D. No. 5.

16. A nucleic acid according to claim 3, wherein said product is an epitope capable of reacting with antibodies, thereby causing an immune reaction resulting in rejection of the cell.

17. A nucleic acid according to claim 3, wherein said product is a Gal α(1,3)-Gall epitope capable of reacting with antibodies, thereby causing an immune reaction resulting in rejection of the cell.

18. A nucleic acid encoding:
   a first porcine Se glycosyltransferase comprising SEQ ID No.6 that:
   i) catalyses transfer of a fucosyl residue to a Galβ(1, 3)GlcNac acceptor substrate, and
   ii) when coexpressed with a second glycosyltransferase in a cell results in reduced levels of a product formed from said acceptor substrait by said second glycosyltransferase, when compared with the level of said product in a cell wherein the porcine Se glycosyltransferase is not expressed.

\* \* \* \* \*

SEQUENCE LISTING

<160> NUMBER OF SEQ ID NOS: 12

<210> SEQ ID NO 1
<211> LENGTH: 26
<212> TYPE: DNA
<213> ORGANISM: Sus scrofa

<400> SEQUENCE: 1
cagaagctta tgctcagcat gcaggc                                      26

<210> SEQ ID NO 2
<211> LENGTH: 27
<212> TYPE: DNA
<213> ORGANISM: Sus scrofa

<400> SEQUENCE: 2
gtcctgcagt gagtgcttaa ggagtgg                                     27

<210> SEQ ID NO 3
<211> LENGTH: 33
<212> TYPE: DNA
<213> ORGANISM: Sus scrofa

<400> SEQUENCE: 3
catgcggccg ctcagtgctt aaggagtggg gac                              33

<210> SEQ ID NO 4
<211> LENGTH: 33
<212> TYPE: DNA
<213> ORGANISM: Sus scrofa

<400> SEQUENCE: 4
gagtcgcgaa tgctcagcat gcaggcatct ttc                              33

<210> SEQ ID NO 5
<211> LENGTH: 1043
<212> TYPE: DNA
<213> ORGANISM: Sus scrofa

<400> SEQUENCE: 5
ctacagccat gctcagcatg caggcatcct tcttcttccc cacgggtccc t tcatcctct      60 ttgtcttcac ggcttccacc atatttcacc ttcagcagag gatggtgaag a ttcaaccca    120 cgtgggagtt acagatggtg acgcaggtga ccacagagag ccctcgagc c cccagctga    180 agggcatgtg gacgatcaat gccatcggcc gcctggggaa ccagatgggg g agtacgcca    240 ccctgtacgc gctggccagg atgaacgggc ggccggcctt catcccgccc g agatgcaca    300 gcacgctggc cccatcttc aggatcaccc tcccggtcct gcacgccagc a cggcccgca    360 ggatcccctg gcagaactac cacctgaacg actggatgga ggagcggtac c gccacatcc    420 cgggggagta cgtgcgcctc acgggctacc cctgctcctg gaccttctac c accacctgc    480

```
gcaccgagat cctccgggag ttcaccctgc ataaccacgt gcgcgaggag g cccaggatt    540 tcctgcgggg tctgcgggtg aacgggagcc gaccgagtac ctacgtgggg g tgcacgtgc    600 gccgggggga ctacgtgcac gtgatgccca acgtgtggaa gggcgtggtg g ccgaccggc   660 ggtacctgga gcaggccctg gactggttcc gggctcgcta ccgctccccc g tctttgtgg   720 tctccagcaa cggcatggcc tggtgtcggg aaaacatcaa tgcctcgcgc g gcgatgtgg   780 tgtttgccgg caatggcatc gagggctccc ccgccaaaga cttcgcgctg c tcacgcagt   840 gtaaccacac tgtcatgacc attggcacgt tcgggatctg gccgcctac c ttgctggtg    900 gagagaccat ctacctggcc aattacacgc tcccggactc tcccttcctc a aactctttta  960 agcccgaggc agccttcctg cccgagtgga ttgggatcga ggcagacctg t ccccactcc  1020 ttaagcactg atgtcggctg tcc                                             1043
```

<210> SEQ ID NO 6
<211> LENGTH: 340
<212> TYPE: PRT
<213> ORGANISM: Sus scrofa

<400> SEQUENCE: 6

```
Met Leu Ser Met Gln Ala Ser Phe Phe P ro Thr Gly Pro Phe Ile
 1               5                  10                  15

Leu Phe Val Phe Thr Ala Ser Thr Ile Phe H is Leu Gln Gln Arg Met
                20                  25                  30

Val Lys Ile Gln Pro Thr Trp Glu Leu Gln M et Val Thr Gln Val Thr
            35                  40                  45

Thr Glu Ser Pro Ser Ser Pro Gln Leu Lys G ly Met Trp Thr Ile Asn
        50                  55                  60

Ala Ile Gly Arg Leu Gly Asn Gln Met Gly G lu Tyr Ala Thr Leu Tyr
 65                  70                  75                  80

Ala Leu Ala Arg Met Asn Gly Arg Pro Ala P he Ile Pro Pro Glu Met
                85                  90                  95

His Ser Thr Leu Ala Pro Ile Phe Arg Ile T hr Leu Pro Val Leu His
            100                 105                 110

Ala Ser Thr Ala Arg Arg Ile Pro Trp Gln A sn Tyr His Leu Asn Asp
        115                 120                 125

Trp Met Glu Glu Arg Tyr Arg His Ile Pro G ly Glu Tyr Val Arg Leu
    130                 135                 140

Thr Gly Tyr Pro Cys Ser Trp Thr Phe Tyr H is His Leu Arg Thr Glu
145                 150                 155                 160

Ile Leu Arg Glu Phe Thr Leu His Asn His V al Arg Glu Glu Ala Gln
                165                 170                 175

Asp Phe Leu Arg Gly Leu Arg Val Asn Gly S er Arg Pro Ser Thr Tyr
            180                 185                 190

Val Gly Val His Val Arg Arg Gly Asp Tyr V al His Val Met Pro Asn
        195                 200                 205

Val Trp Lys Gly Val Val Ala Asp Arg Arg T yr Leu Glu Gln Ala Leu
    210                 215                 220

Asp Trp Phe Arg Ala Arg Tyr Arg Ser Pro V al Phe Val Val Ser Ser
225                 230                 235                 240

Asn Gly Met Ala Trp Cys Arg Glu Asn Ile A sn Ala Ser Arg Gly Asp
                245                 250                 255

Val Val Phe Ala Gly Asn Gly Ile Glu Gly S er Pro Ala Lys Asp Phe
            260                 265                 270
```

-continued

Ala Leu Leu Thr Gln Cys Asn His Thr Val Met Thr Ile Gly Thr Phe
        275                 280                 285

Gly Ile Trp Ala Ala Tyr Leu Ala Gly Gly Glu Thr Ile Tyr Leu Ala
    290                 295                 300

Asn Tyr Thr Leu Pro Asp Ser Pro Phe Leu Lys Leu Phe Lys Pro Glu
305                 310                 315                 320

Ala Ala Phe Leu Pro Glu Trp Ile Gly Ile Glu Ala Asp Leu Ser Pro
            325                 330                 335

Leu Leu Lys His
        340

<210> SEQ ID NO 7
<211> LENGTH: 340
<212> TYPE: PRT
<213> ORGANISM: Sus scrofa

<400> SEQUENCE: 7

Met Leu Ser Met Gln Ala Ser Phe Phe Pro Thr Gly Pro Phe Ile
1               5                   10                  15

Leu Phe Val Phe Thr Ala Ser Thr Ile Phe His Leu Gln Gln Arg Met
            20                  25                  30

Val Lys Ile Gln Pro Thr Trp Glu Leu Gln Met Val Thr Gln Val Thr
        35                  40                  45

Thr Glu Ser Pro Ser Ser Pro Gln Leu Lys Gly Met Trp Thr Ile Asn
    50                  55                  60

Ala Ile Gly Arg Leu Gly Asn Gln Met Gly Glu Tyr Ala Thr Leu Tyr
65              70                  75                  80

Ala Leu Ala Arg Met Asn Gly Arg Pro Ala Phe Ile Pro Pro Glu Met
                85                  90                  95

His Ser Thr Leu Ala Pro Ile Phe Arg Ile Thr Leu Pro Val Leu His
            100                 105                 110

Ala Ser Thr Ala Arg Arg Ile Pro Trp Gln Asn Tyr His Leu Asn Asp
        115                 120                 125

Trp Met Glu Glu Arg Tyr Arg His Ile Pro Gly Glu Tyr Val Arg Leu
    130                 135                 140

Thr Gly Tyr Pro Cys Ser Trp Thr Phe Tyr His His Leu Arg Thr Glu
145                 150                 155                 160

Ile Leu Arg Glu Phe Thr Leu His Asn His Val Arg Glu Glu Ala Gln
                165                 170                 175

Asp Phe Leu Arg Gly Leu Arg Val Asn Gly Ser Arg Pro Ser Thr Tyr
            180                 185                 190

Val Gly Val His Val Arg Arg Gly Asp Tyr Val His Val Met Pro Asn
        195                 200                 205

Val Trp Lys Gly Val Val Ala Asp Arg Arg Tyr Leu Glu Gln Ala Leu
    210                 215                 220

Asp Trp Phe Arg Ala Arg Tyr Arg Ser Pro Val Phe Val Val Ser Ser
225                 230                 235                 240

Asn Gly Met Ala Trp Cys Arg Glu Asn Ile Asn Ala Ser Arg Gly Asp
                245                 250                 255

Val Val Phe Ala Gly Asn Gly Ile Glu Gly Ser Pro Ala Lys Asp Phe
            260                 265                 270

Ala Leu Leu Thr Gln Cys Asn His Thr Val Met Thr Ile Gly Thr Phe
        275                 280                 285

Gly Ile Trp Ala Ala Tyr Leu Ala Gly Gly Glu Thr Ile Tyr Leu Ala

```
                    290                 295                 300
Asn Tyr Thr Leu Pro Asp Ser Pro Phe Leu L ys Leu Phe Lys Pro Glu
305                 310                 315                 320

Ala Ala Phe Leu Pro Glu Trp Ile Gly Ile G lu Ala Asp Leu Ser Pro
                    325                 330                 335

Leu Leu Lys His
            340

<210> SEQ ID NO 8
<211> LENGTH: 343
<212> TYPE: PRT
<213> ORGANISM: Homo sapiens

<400> SEQUENCE: 8

Met Leu Val Val Gln Met Pro Phe Ser Phe P ro Met Ala His Phe Ile
  1               5                  10                  15

Leu Phe Val Phe Thr Val Ser Thr Ile Phe H is Val Gln Arg Leu
             20                  25                  30

Ala Lys Ile Gln Ala Met Trp Glu Leu Pro V al Gln Ile Pro Val Leu
            35                  40                  45

Ala Ser Thr Ser Lys Ala Leu Gly Pro Ser G ln Leu Arg Gly Met Trp
         50                  55                  60

Thr Ile Asn Ala Ile Gly Arg Leu Gly Asn G ln Met Gly Glu Tyr Ala
 65                  70                  75                  80

Thr Leu Tyr Ala Leu Ala Lys Met Asn Gly A rg Pro Ala Phe Ile Pro
                 85                  90                  95

Ala Gln Met His Ser Thr Leu Ala Pro Ile P he Arg Ile Thr Leu Pro
                100                 105                 110

Val Leu His Ser Ala Thr Ala Ser Arg Ile P ro Trp Gln Asn Tyr His
            115                 120                 125

Leu Asn Asp Trp Met Glu Glu Glu Tyr Arg H is Ile Pro Gly Glu Tyr
    130                 135                 140

Val Arg Phe Thr Gly Tyr Pro Cys Ser Trp T hr Phe Tyr His His Leu
145                 150                 155                 160

Arg Gln Glu Ile Leu Gln Glu Phe Thr Leu H is Asp His Val Arg Glu
                165                 170                 175

Glu Ala Gln Lys Phe Leu Arg Gly Leu Gln V al Asn Gly Ser Arg Pro
            180                 185                 190

Gly Thr Phe Val Gly Val His Val Arg Arg G ly Asp Tyr Val His Val
        195                 200                 205

Met Pro Lys Val Trp Lys Gly Val Val Ala A sp Arg Arg Tyr Leu Gln
210                 215                 220

Gln Ala Leu Asp Trp Phe Arg Ala Arg Tyr S er Ser Leu Ile Phe Val
225                 230                 235                 240

Val Thr Ser Asn Gly Met Ala Trp Cys Arg G lu Asn Ile Asp Thr Ser
                245                 250                 255

His Gly Asp Val Val Phe Ala Gly Asp Gly I le Glu Gly Ser Pro Ala
            260                 265                 270

Lys Asp Phe Ala Leu Leu Thr Gln Cys Asn H is Thr Ile Met Thr Ile
        275                 280                 285

Gly Thr Phe Gly Ile Trp Ala Ala Tyr Leu T hr Gly Gly Asp Thr Ile
    290                 295                 300

Tyr Leu Ala Asn Tyr Thr Leu Pro Asp Ser P ro Phe Leu Lys Ile Phe
305                 310                 315                 320
```

Lys Pro Glu Ala Ala Phe Leu Pro Glu Trp Thr Gly Ile Ala Ala Asp
             325                 330                 335

Leu Ser Pro Leu Leu Lys His
             340

<210> SEQ ID NO 9
<211> LENGTH: 347
<212> TYPE: PRT
<213> ORGANISM: Lepus Sp.

<400> SEQUENCE: 9

Met Ser Thr Ala Gln Val Pro Phe Ala Phe Pro Met Val His Val Ile
  1               5                  10                  15

Leu Phe Val Phe Thr Ala Ser Thr Ile Phe His Leu Gln Gln Arg Leu
                 20                  25                  30

Val Arg Ile Gln Pro Thr Trp Glu Glu Leu Leu Pro Ala Leu Thr Pro
             35                  40                  45

Ala Val Thr Phe Arg Pro Thr Ser Gln Arg Ala Pro Ser Arg Pro Leu
         50                  55                  60

Gly Gly Met Trp Thr Ile Asn Ala Met Gly Arg Leu Gly Asn Gln Met
 65                  70                  75                  80

Gly Glu Tyr Ala Thr Leu Tyr Ala Leu Ala Lys Glu Asn Gly Arg Pro
                 85                  90                  95

Ala Tyr Ile Pro Ala Gln Met His Ser Thr Leu Ala Pro Ile Phe Arg
            100                 105                 110

Ile Ser Leu Pro Val Leu His Ser Ser Thr Ala Ser Arg Val Pro Trp
            115                 120                 125

Gln Asn Tyr His Leu Asn Asp Trp Met Glu Glu Arg Tyr Arg His Ile
        130                 135                 140

Pro Ala Pro Tyr Val Arg Leu Thr Gly Tyr Pro Cys Ser Trp Thr Phe
145                 150                 155                 160

Tyr His His Leu Arg His Glu Ile Leu Arg Glu Phe Thr Leu His Asp
                165                 170                 175

His Val Arg Glu Glu Ala Gln Ala Phe Leu Arg Gly Leu Arg Val Asn
            180                 185                 190

Gly Ser Arg Pro Ser Thr Phe Val Gly Val His Val Arg Arg Gly Asp
        195                 200                 205

Tyr Val Arg Val Met Pro Gln Val Trp Lys Gly Val Val Ala Asp Arg
    210                 215                 220

Gly Tyr Leu Glu Gln Ala Leu Asp Trp Phe Arg Ala Arg Tyr Arg Ser
225                 230                 235                 240

Pro Val Phe Val Val Thr Ser Asn Gly Met Ala Trp Cys Arg Glu Met
                245                 250                 255

Ile Asp Ala Ser Arg Gly Asp Val Phe Ala Gly Met Gly Leu Glu
            260                 265                 270

Ser Ser Pro Ala Lys Asp Phe Ala Leu Leu Thr Gln Val Asn His Thr
        275                 280                 285

Val Met Thr Ile Gly Thr Phe Gly Ile Trp Ala Ala Tyr Leu Thr Gly
    290                 295                 300

Gly Asp Thr Ile Tyr Leu Ala Asn Tyr Thr Leu Pro Asp Ser Pro Phe
305                 310                 315                 320

Leu Lys Ile Phe Lys Pro Glu Ala Ala Phe Leu Pro Glu Trp Val Gly
                325                 330                 335

Ile Asn Ala Asp Leu Ser Pro Leu Leu Lys His
            340                 345

```
<210> SEQ ID NO 10
<211> LENGTH: 365
<212> TYPE: PRT
<213> ORGANISM: Sus scrofa

<400> SEQUENCE: 10

Met Trp Val Pro Ser Arg Arg His Leu Cys Leu Thr Phe Leu Leu Val
 1               5                  10                  15

Cys Val Leu Ala Ala Ile Phe Phe Leu Asn Val Tyr Gln Asp Leu Phe
             20                  25                  30

Tyr Ser Gly Leu Asp Leu Leu Ala Leu Cys Pro Asp His Asn Val Val
         35                  40                  45

Ser Ser Pro Val Ala Ile Phe Cys Leu Ala Gly Thr Pro Val His Pro
     50                  55                  60

Asn Ala Ser Asp Ser Cys Pro Lys His Pro Ala Ser Phe Ser Gly Thr
 65                  70                  75                  80

Trp Thr Ile Tyr Pro Asp Gly Arg Phe Gly Asn Gln Met Gly Gln Tyr
                 85                  90                  95

Ala Thr Leu Leu Ala Leu Ala Gln Leu Asn Gly Arg Gln Ala Phe Ile
            100                 105                 110

Gln Pro Ala Met His Ala Val Leu Ala Pro Val Phe Arg Ile Thr Leu
        115                 120                 125

Pro Val Leu Ala Pro Glu Val Asp Arg His Ala Pro Trp Arg Glu Leu
130                 135                 140

Glu Leu His Asp Trp Met Ser Glu Asp Tyr Ala His Leu Lys Glu Pro
145                 150                 155                 160

Trp Leu Lys Leu Thr Gly Phe Pro Cys Ser Trp Thr Phe Phe His His
                165                 170                 175

Leu Arg Glu Gln Ile Arg Ser Glu Phe Thr Leu His Asp His Leu Arg
            180                 185                 190

Gln Glu Ala Gln Gly Val Leu Ser Gln Phe Arg Leu Pro Arg Thr Gly
        195                 200                 205

Asp Arg Pro Ser Thr Phe Val Gly Val His Val Arg Arg Gly Asp Tyr
    210                 215                 220

Leu Arg Val Met Pro Lys Arg Trp Lys Gly Val Val Gly Asp Gly Ala
225                 230                 235                 240

Tyr Leu Gln Gln Ala Met Asp Trp Phe Arg Ala Arg Tyr Glu Ala Pro
                245                 250                 255

Val Phe Val Val Thr Ser Asn Gly Met Glu Trp Cys Arg Lys Asn Ile
            260                 265                 270

Asp Thr Ser Arg Gly Asp Val Ile Phe Ala Gly Asp Gly Arg Glu Ala
        275                 280                 285

Ala Pro Ala Arg Asp Phe Ala Leu Leu Val Gln Cys Asn His Thr Ile
    290                 295                 300

Met Thr Ile Gly Thr Phe Gly Phe Trp Ala Ala Tyr Leu Ala Gly Gly
305                 310                 315                 320

Asp Thr Ile Tyr Leu Ala Asn Phe Thr Leu Pro Thr Ser Ser Phe Leu
                325                 330                 335

Lys Ile Phe Lys Pro Glu Ala Ala Phe Leu Pro Glu Trp Val Gly Ile
            340                 345                 350

Asn Ala Asp Leu Ser Pro Leu Gln Met Leu Ala Gly Pro
        355                 360                 365
```

```
<210> SEQ ID NO 11
<211> LENGTH: 365
<212> TYPE: PRT
<213> ORGANISM: Homo sapiens

<400> SEQUENCE: 11
```

| Met | Trp | Leu | Arg | Ser | His | Arg | Gln | Leu | Cys | Leu | Ala | Phe | Leu | Leu | Val |
|---|---|---|---|---|---|---|---|---|---|---|---|---|---|---|---|
| 1 | | | | 5 | | | | | 10 | | | | | 15 | |

| Cys | Val | Leu | Ser | Val | Ile | Phe | Phe | Leu | His | Ile | His | Gln | Asp | Ser | Phe |
|---|---|---|---|---|---|---|---|---|---|---|---|---|---|---|---|
| | | | 20 | | | | | 25 | | | | | 30 | | |

| Pro | His | Gly | Leu | Gly | Leu | Ser | Ile | Leu | Cys | Pro | Asp | Arg | Arg | Leu | Val |
| | | 35 | | | | | 40 | | | | | 45 | | | |

| Thr | Pro | Pro | Val | Ala | Ile | Phe | Cys | Leu | Pro | Gly | Thr | Ala | Met | Gly | Pro |
| | 50 | | | | | 55 | | | | | 60 | | | | |

| Asn | Ala | Ser | Ser | Cys | Pro | Gln | His | Pro | Ala | Ser | Leu | Ser | Gly | Thr |
| 65 | | | | 70 | | | | | 75 | | | | | 80 |

| Trp | Thr | Val | Tyr | Pro | Asn | Gly | Arg | Phe | Gly | Asn | Gln | Met | Gly | Gln | Tyr |
| | | | | 85 | | | | | 90 | | | | | 95 | |

| Ala | Thr | Leu | Leu | Ala | Leu | Ala | Gln | Leu | Asn | Gly | Arg | Arg | Ala | Phe | Ile |
| | | | 100 | | | | | 105 | | | | | 110 | | |

| Leu | Pro | Ala | Met | His | Ala | Ala | Leu | Ala | Pro | Val | Phe | Arg | Ile | Thr | Leu |
| | | | 115 | | | | | 120 | | | | | 125 | | |

| Pro | Val | Leu | Ala | Pro | Glu | Val | Asp | Ser | Arg | Thr | Pro | Trp | Arg | Glu | Leu |
| | 130 | | | | | 135 | | | | | 140 | | | | |

| Gln | Leu | His | Asp | Trp | Met | Ser | Glu | Glu | Tyr | Ala | Asp | Leu | Arg | Asp | Pro |
| 145 | | | | | 150 | | | | | 155 | | | | | 160 |

| Phe | Leu | Lys | Leu | Ser | Gly | Phe | Pro | Cys | Ser | Trp | Thr | Phe | Phe | His | His |
| | | | | 165 | | | | | 170 | | | | | 175 | |

| Leu | Arg | Glu | Gln | Ile | Arg | Arg | Gly | Phe | Thr | Leu | His | Asp | His | Leu | Arg |
| | | | 180 | | | | | 185 | | | | | 190 | | |

| Glu | Glu | Ala | Gln | Ser | Val | Leu | Gly | Gln | Leu | Arg | Leu | Gly | Arg | Thr | Gly |
| | | | 195 | | | | | 200 | | | | | 205 | | |

| Asp | Arg | Pro | Arg | Thr | Phe | Val | Gly | Val | His | Val | Arg | Arg | Gly | Asp | Tyr |
| | 210 | | | | | 215 | | | | | 220 | | | | |

| Leu | Gln | Val | Met | Pro | Gln | Arg | Trp | Lys | Gly | Val | Val | Gly | Asp | Ser | Ala |
| 225 | | | | | 230 | | | | | 235 | | | | | 240 |

| Tyr | Leu | Arg | Gln | Ala | Met | Asp | Trp | Phe | Arg | Ala | Arg | His | Glu | Ala | Pro |
| | | | | 245 | | | | | 250 | | | | | 255 | |

| Val | Phe | Val | Val | Thr | Ser | Asn | Gly | Met | Glu | Trp | Cys | Lys | Glu | Asn | Ile |
| | | | 260 | | | | | 265 | | | | | 270 | | |

| Asp | Thr | Ser | Gln | Gly | Asp | Val | Thr | Phe | Ala | Gly | Asp | Gly | Gln | Glu | Ala |
| | | | 275 | | | | | 280 | | | | | 285 | | |

| Thr | Pro | Trp | Lys | Asp | Phe | Ala | Leu | Leu | Thr | Gln | Cys | Asn | His | Thr | Ile |
| | | 290 | | | | | 295 | | | | | 300 | | | |

| Met | Thr | Ile | Gly | Thr | Phe | Gly | Phe | Trp | Ala | Ala | Tyr | Leu | Ala | Gly | Gly |
| 305 | | | | | 310 | | | | | 315 | | | | | 320 |

| Asp | Thr | Val | Tyr | Leu | Ala | Asn | Phe | Thr | Leu | Pro | Asp | Ser | Glu | Phe | Leu |
| | | | | 325 | | | | | 330 | | | | | 335 | |

| Lys | Ile | Phe | Lys | Pro | Glu | Ala | Ala | Phe | Leu | Pro | Glu | Trp | Val | Gly | Ile |
| | | | 340 | | | | | 345 | | | | | 350 | | |

| Asn | Ala | Asp | Leu | Ser | Pro | Leu | Trp | Thr | Leu | Ala | Lys | Pro |
| | | | 355 | | | | | 360 | | | | | 365 |

<210> SEQ ID NO 12
<211> LENGTH: 373
<212> TYPE: PRT
<213> ORGANISM: Lepus Sp.

<400> SEQUENCE: 12

```
Met Trp Pro Pro Ser Arg Arg Gln Leu Cys Leu Ala Phe Leu Leu Val
 1               5                  10                  15

Cys Ala Leu Ser Ala Phe Ser Phe Leu Leu His Leu His Gln Asp Leu
             20                  25                  30

Phe Arg Asn Gly Leu Ala Leu Ser Leu Pro Cys Leu Glu Arg Gln Pro
         35                  40                  45

Val Pro Ala Pro Val Ala Ile Val Cys Leu Pro Val Thr Ser Pro Ala
     50                  55                  60

Ser Asn Ala Ser Ser Cys Ala Gly Arg Pro Ala Ala Pro Ser Gly Ile
 65                  70                  75                  80

Trp Thr Ile His Pro Asp Gly Arg Phe Gly Asn Gln Met Gly Gln Tyr
                 85                  90                  95

Ala Thr Leu Leu Ala Leu Ala Gln Leu Asn Gly Arg Arg Ala Phe Ile
            100                 105                 110

Leu Pro Ala Met His Ala Ala Leu Ala Pro Val Phe Arg Ile Thr Leu
        115                 120                 125

Pro Val Leu Ala Pro Glu Val Asn Arg Arg Thr Ser Trp Lys Gln Leu
    130                 135                 140

Leu Leu His Asp Trp Met Ser Glu Glu Tyr Ser Arg Leu Glu Asp Pro
145                 150                 155                 160

Phe Leu Lys Phe Thr Gly Phe Pro Cys Ser Trp Thr Phe Phe His His
                165                 170                 175

Val Arg Glu Gln Ile Arg Arg Glu Phe Thr Leu His Asp His Leu Arg
            180                 185                 190

Glu Glu Ala Gln Arg Leu Leu Gly Lys Leu Arg Leu Gly Arg Thr Gly
        195                 200                 205

Ala Arg Pro Arg Thr Phe Val Gly Val His Val Arg Arg Gly Asp Tyr
    210                 215                 220

Leu Gln Val Met Pro Gln Arg Trp Lys Gly Val Val Gly Asp Arg Ala
225                 230                 235                 240

Tyr Leu Gln Gln Ala Met Asp Trp Phe Arg Ala Arg His Glu Ala Pro
                245                 250                 255

Ile Phe Val Val Thr Ser Asn Gly Met Lys Trp Cys Trp Glu Asn Ile
            260                 265                 270

Asp Ala Ser Arg Gly Asp Val Val Phe Ala Gly Asn Gly Leu Glu Ser
        275                 280                 285

Ser Pro Ala Lys Asp Phe Ala Leu Leu Thr Gln Cys Asn His Thr Val
    290                 295                 300

Met Thr Ile Gly Thr Phe Gly Phe Trp Ala Ala Tyr Leu Ala Gly Gly
305                 310                 315                 320

Asp Thr Val Tyr Leu Ala Asn Phe Thr Leu Pro Asp Ser Glu Phe Leu
                325                 330                 335

Lys Ile Phe Lys Pro Glu Ala Ala Phe Leu Pro Glu Trp Val Gly Ile
            340                 345                 350
```

-continued

```
Asn Ala Asp Leu Ser Pro Val Arg Thr Leu S er Gly Ser Trp Arg Pro
            355                 360             365
Trp Arg Phe Leu Gly
    370
```